United States Patent
Hara et al.

(10) Patent No.: US 10,364,900 B2
(45) Date of Patent: Jul. 30, 2019

(54) FLUID SWITCHING VALVE AND LIQUID CHROMATOGRAPH APPARATUS USING THE SAME

(71) Applicant: Hitachi High-Technologies Corporation, Minato-ku, Tokyo (JP)

(72) Inventors: Takaaki Hara, Tokyo (JP); Hiroshi Moriya, Tokyo (JP); Ayano Otsubo, Tokyo (JP); Yoshihiro Nagaoka, Tokyo (JP); Kiyotoshi Mori, Tokyo (JP); Shoji Tomita, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 196 days.

(21) Appl. No.: 15/038,895

(22) PCT Filed: Jan. 22, 2015

(86) PCT No.: PCT/JP2015/051603
§ 371 (c)(1),
(2) Date: May 24, 2016

(87) PCT Pub. No.: WO2015/122253
PCT Pub. Date: Aug. 20, 2015

(65) Prior Publication Data
US 2016/0377184 A1 Dec. 29, 2016

(30) Foreign Application Priority Data

Feb. 12, 2014 (JP) .................................. 2014-023966

(51) Int. Cl.
*F16K 3/06* (2006.01)
*G01N 30/20* (2006.01)
(Continued)

(52) U.S. Cl.
CPC ............ *F16K 3/06* (2013.01); *F16K 11/0743* (2013.01); *G01N 30/20* (2013.01); *G01N 30/26* (2013.01);
(Continued)

(58) Field of Classification Search
None
See application file for complete search history.

(56) References Cited

U.S. PATENT DOCUMENTS

| | | | | |
|---|---|---|---|---|
| 3,203,249 | A * | 8/1965 | Jentzsch | G01N 30/20 137/625.21 |
| 4,444,066 | A * | 4/1984 | Ogle | G01N 30/20 73/61.56 |
| 4,501,297 | A * | 2/1985 | Baker | F16K 31/042 137/554 |
| 5,920,006 | A * | 7/1999 | Zelechonok | F04B 7/0007 73/61.55 |

(Continued)

FOREIGN PATENT DOCUMENTS

| | | |
|---|---|---|
| JP | 2008-215494 A | 9/2008 |
| WO | WO 2009/101695 A1 | 8/2009 |
| WO | WO 2012/109103 A2 | 8/2012 |

OTHER PUBLICATIONS

International Search Report (PCT/ISA/210) issued in PCT Application No. PCT/JP2015/051603 dated Apr. 7, 2015 with English translation (Two (2) pages).

(Continued)

*Primary Examiner* — John Fox
(74) *Attorney, Agent, or Firm* — Crowell & Moring LLP (57) ABSTRACT

Provided are: a flow path switching valve that reduces the pressure load in a contact surface outer peripheral section of the flow path switching valve and inhibits friction between constituent components; and a liquid chromatographic device using the flow path switching valve. The flow path (Continued)

switching valve is provided with a stator having a plurality of through holes and a seal having conduction grooves for causing the through holes to conduct. The seal has a first portion present vertically beneath a region comprising at least a surface of contact with the stator, and a second portion having lower rigidity than the first portion, on the outside of the first portion. Due to this configuration, it is possible to reduce the pressure load when a flow path of a liquid is switched under high-pressure conditions, and inhibit the phenomenon of friction itself.

7 Claims, 13 Drawing Sheets

(51) Int. Cl.
*F16K 11/074* (2006.01)
*G01N 30/26* (2006.01)
*G01N 30/38* (2006.01)

(52) U.S. Cl.
CPC . *G01N 2030/202* (2013.01); *G01N 2030/385* (2013.01)

(56) References Cited

U.S. PATENT DOCUMENTS

| | | | | |
|---|---|---|---|---|
| 6,193,213 | B1* | 2/2001 | Stearns | F16K 3/10 |
| | | | | 137/625.46 |
| 9,188,238 | B2* | 11/2015 | Tanaka | F16K 31/042 |
| 9,316,324 | B2* | 4/2016 | Berndt | F16K 11/074 |
| 9,939,415 | B2* | 4/2018 | Hochgraeber | F16K 11/0743 |
| 2010/0276617 | A1 | 11/2010 | Yasunaga | |
| 2012/0119127 | A1* | 5/2012 | Tower | F16K 3/08 |
| | | | | 251/304 |
| 2014/0007660 | A1 | 1/2014 | Moeller et al. | |

OTHER PUBLICATIONS

Japanese-language Written Opinion (PCT/ISA/237) issued in PCT Application No. PCT/JP2015/051603 dated Apr. 7, 2015 (Three (3) pages).

* cited by examiner

Prior Art

FLUID SWITCHING VALVE AND LIQUID CHROMATOGRAPH APPARATUS USING THE SAME

TECHNICAL FIELD

The present invention relates to a fluid switching valve that switches a flow path of liquid. Further, the present invention relates to a liquid chromatograph apparatus and a liquid chromatograph system using the fluid switching valve.

BACKGROUND ART

In most products in an analyzer for liquid, a fluid switching valve that switches a flow path of liquid is used. For example, in a liquid chromatograph apparatus, a fluid switching valve that switches a flow path under high-pressure conditions is used in order to transport a sample as an analysis subject, which is introduced into a mobile phase flow path, to a column for separation of each component.

Figure 16:
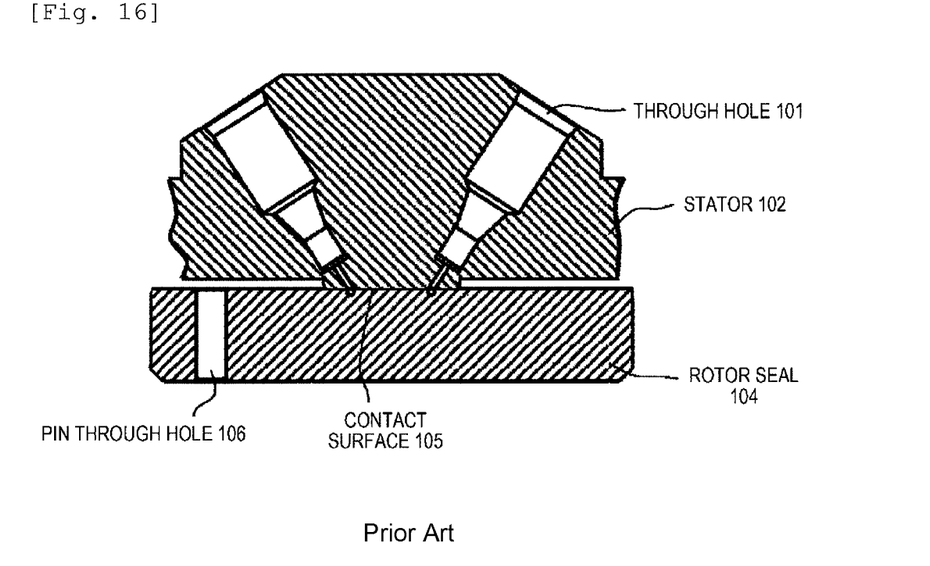
FIG. 16 is a diagram showing a configuration of a fluid switching valve of the related art.

FIG. 16 shows a structure of a general fluid switching valve of the related art. Basically, the fluid switching valve includes: a stator 102 having through holes 101 to which fluid inlet-outlet tubes are connected; and a rotor seal 104 that is connected to the stator 102. The stator 102 and the rotor seal 104 seal a flow path so as to prevent fluid from leaking to the outside while rubbing against each other through a contact surface.

As a countermeasure against the rubbing between the stator and the rotor seal in the fluid switching valve, PTL 1 describes a method of providing a space on a contact surface side of either the stator or the rotor seal to reduce an area where rubbing occurs.

CITATION LIST

Patent Literature

PTL 1: Pamphlet of International Publication No. WO2012/109103

SUMMARY OF INVENTION

Technical Problem

Recently, the speed and volume of a feeding pressure of fluid have increased, and thus a fastening load of a valve has also increased. That is, a load applied to the contact surface between the stator and the rotor seal has increased, and thus the contact surface is more likely to be worn away.

The rotor seal is formed of a material having higher flexibility than a material of the stator in most cases and rotates around the stator. Therefore, in particular, the rotor seal is likely to be worn away. A contact surface outer peripheral portion between the stator and the rotor seal has a long moving distance during rotation, and thus wear debris is likely to be produced. As a result, the contact surface may be further scratched, or the produced wear debris may be incorporated into a flow path.

However, in the technique described in PTL 1, the space is provided in the contact surface to physically reduce the area of the contact surface which may be worn away. However, since the other area of the contact surface is still likely to be worn away, the above-described problem may still occur.

In addition, in PTL 1, the space provided in the contact surface between the stator and the rotor seal requires high processing accuracy during molding such that burrs and the like produced during the formation of the space do not scratch the contact surface during the rotation of the rotor seal. Further, there is limitation in the arrangement of the space. For example, it is necessary that the space is formed at a predetermined distance from a flow path of the stator and the rotor seal.

An object of the present invention is to provide: a fluid switching valve that reduces a rubbing phenomenon occurring between the stator and the rotor seal; and a liquid chromatograph apparatus using the fluid switching valve.

Solution to Problem

As a result of thorough investigation, the present inventors found a configuration which contributes to a reduction in pressure applied to a contact surface between a stator and a rotor seal, the pressure being one of the reasons for the rubbing phenomenon in a fluid switching valve. That is, according to an aspect of the present invention for solving the above-described problems, there are provided a fluid switching valve and a liquid chromatograph apparatus using the fluid switching valve, the fluid switching valve including: a stator having a plurality of through holes; and a seal having a connection groove through which the through holes are connected to each other, in which the seal includes at least a first portion that is present vertically downward with respect to a region containing at least a contact surface with the stator, and a second portion that is provided outside the first portion and has lower rigidity than the first portion.

Advantageous Effects of Invention

According to the aspect, a fluid switching valve and an apparatus using the fluid switching valve can be provided, in which a rubbing phenomenon can be reduced by reducing a pressure applied to a contact surface outer peripheral portion instead of reducing the area of a contact surface between a stator and a rotor seal.

BRIEF DESCRIPTION OF DRAWINGS

FIG. 1-A is a diagram showing an overall configuration example of a fluid switching valve according to an embodiment of the present invention.

FIG. 1-B is a diagram showing a configuration example (first example) of a fluid switching valve according to an embodiment (Embodiment 1) of the present invention.

FIGS. 2-A to 2-C are diagrams showing the reason why a recess according to the embodiment of the present invention reduces a pressure applied to a contact surface outer peripheral portion.

FIG. 7-A is a diagram showing a configuration example (third example) of a fluid switching valve according to an embodiment (Embodiment 2) of the present invention.

FIG. 7-B is a diagram showing a configuration example (fourth example) of the fluid switching valve according to the embodiment (Embodiment 2) of the present invention.

DESCRIPTION OF EMBODIMENTS

Hereinafter, embodiments of the present invention will be described using the drawings.

Embodiment 1

In this embodiment, an example of a fluid switching valve that reduces a pressure applied to a contact surface outer peripheral portion between a stator and a seal will be described.

Figure 1:
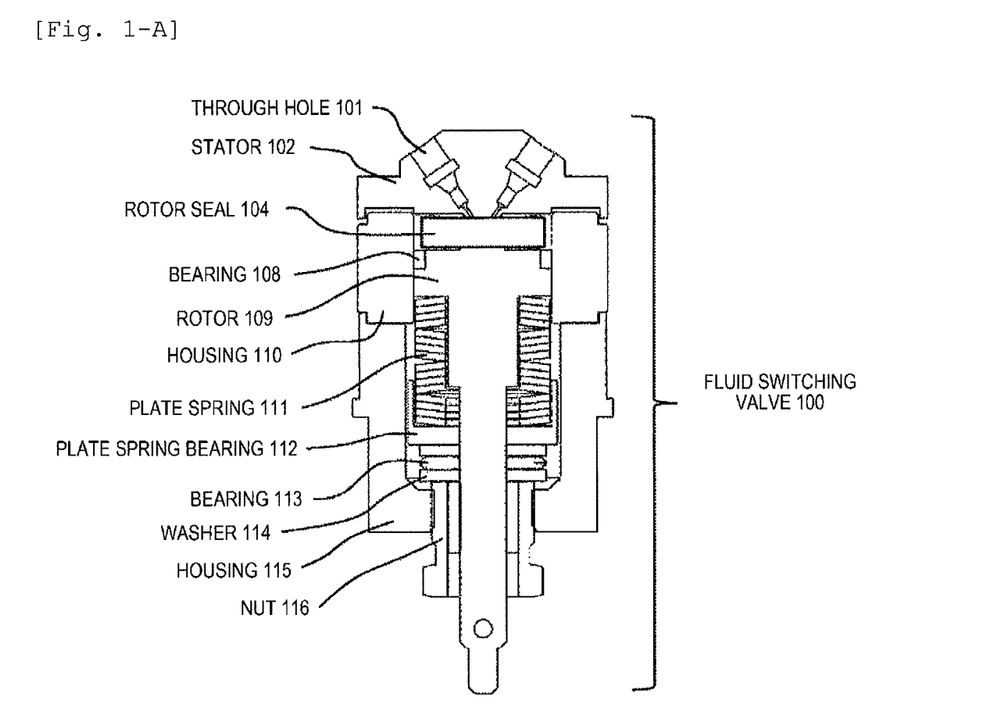

FIG. 1 is a diagram showing a configuration example of the fluid switching valve according to the embodiment of the present invention. FIG. 1-A is an overall configuration diagram of the valve, and FIG. 1-B is a diagram showing a configuration example (first example) of the valve, which is an enlarged cross-sectional view showing contact between a stator and a rotor seal.

The fluid switching valve 100 includes a stator 102, a rotor seal 104, a bearing 108, a rotor 109, a housing 110, a plate spring 111, a plate spring bearing 112, a bearing 113, a washer 114, a housing 115, and a nut 116. The stator 102 includes through holes 101. The rotor seal 104 includes a connection groove 103, a pin through hole 106, and a recess 107 that is formed on a surface of the rotor seal 104 opposite to a contact surface with the stator 102. The rotor seal 104 is arranged so as to be in contact with the stator 102 and is rotatable due to the rotor 109. The stator 102, the housing 110, and the housing 115 are fixed through a screw.

The configuration of the fluid switching valve according to the embodiment is different from the configuration of the fluid switching valve of the related art shown in FIG. 16, in that the recess 107 is provided on the surface of the rotor seal 104 opposite to the contact surface with the stator 102. With the above-described configuration, the pressure applied to the outer peripheral portion of the contact surface 105 can be reduced as described below.

Next, a mechanism will be described using FIG. 2 in which the recess 107 shown in FIG. 1 exhibits an effect of reducing the pressure applied to the outer peripheral portion of the contact surface 105 between the stator 102 and the rotor seal 104.

Figure 2:
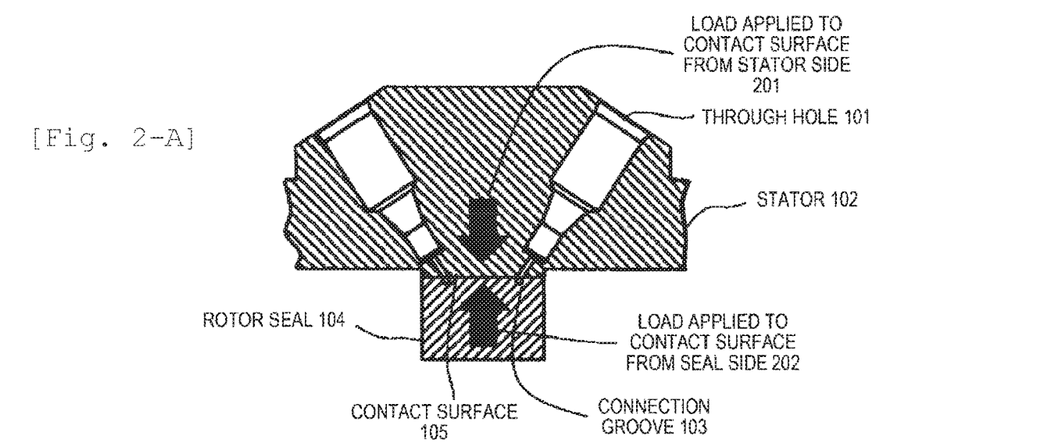

FIG. 2 is a diagram showing the reason why the recess according to the embodiment reduces the pressure applied to the contact surface outer peripheral portion.

The stator 102 and the rotor seal 104 receive a fastening load in the vertical direction in order to prevent liquid leakage from a flow path including the through holes 101 and the connection groove 103. Focusing on a relationship between the stator 102 and the rotor seal 104, this load is balanced on the contact surface 105. Therefore, when the top surface of the rotor seal 104 has the same shape (area) as that of the contact surface 105 as shown in FIG. 2(A), a load 201 on the stator 102 side and a load 202 on the rotor seal 104 side are well-balanced in the contact surface 105. However, as shown in FIG. 2(B), according to the shape of the existing rotor seal 104, the entire area of the top surface is wider than that of the contact surface 105. Therefore, a load 203 is newly added to the load 201 applied from the stator 102 side such that the load 201 is supported in a contact surface outer peripheral portion 117 which is a region of the top surface of the rotor seal 104 positioned outside of the contact surface 105. As a result, the contact surface outer peripheral portion 117 is likely to be worn away because a higher load is applied thereto than the center of the contact surface 105.

Therefore, as shown in FIG. 2(C), the rotor seal 104 has a structure in which the recess 107 is provided on the surface of the rotor seal 104 opposite to the contact surface and in which a region that is present vertically downward with respect to a region containing at least the contact surface has higher rigidity than the other peripheral region. With the above-described structure, a seal member in the peripheral region can be reduced, the seal member is likely to be deformed, and the magnitude of the load 203 can be reduced as compared to FIG. 2(B).

Figure 3:
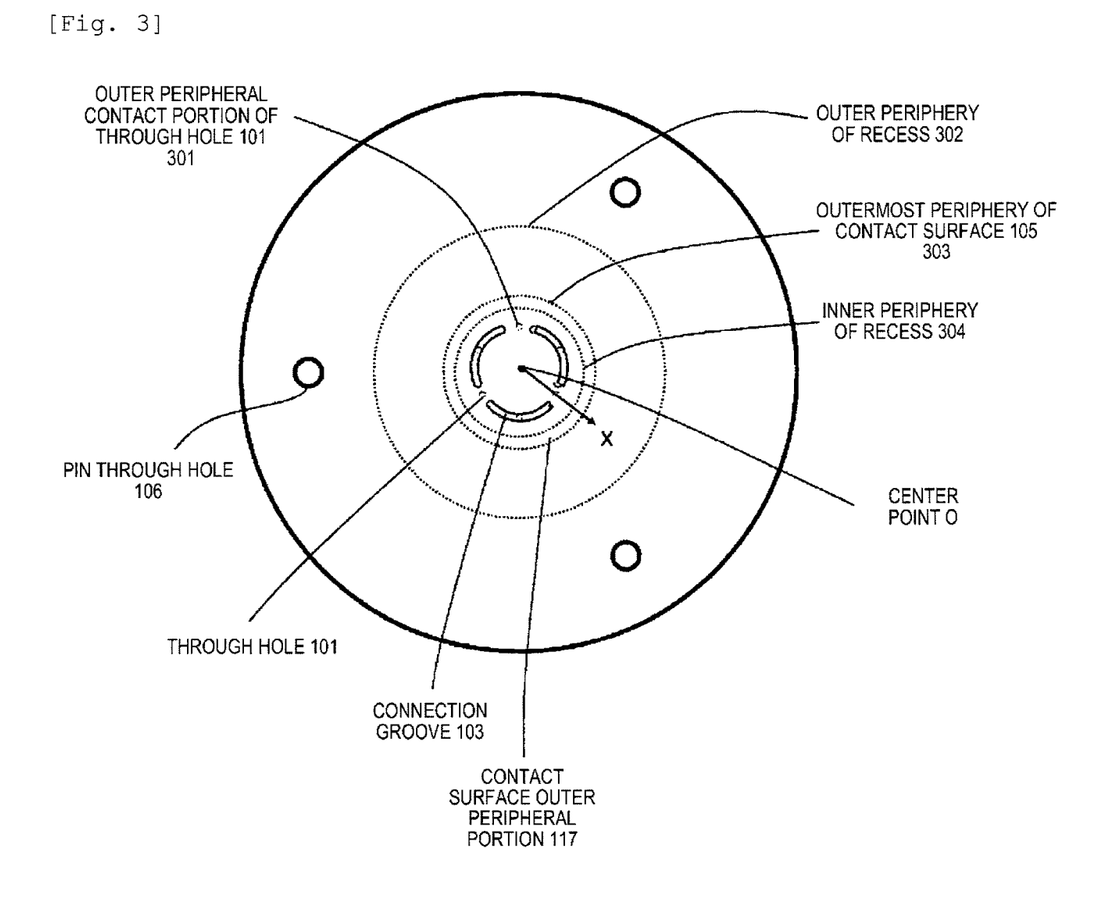
FIG. 3 is a diagram showing a top surface of a rotor seal according to the embodiment of the present invention.
Figure 4:
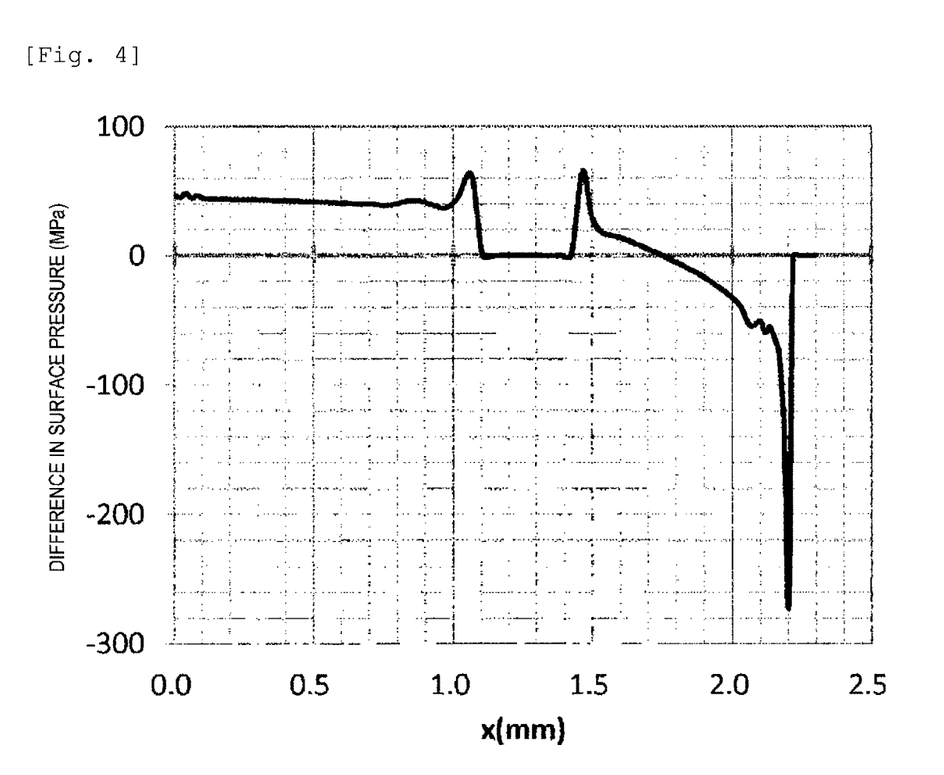
FIG. 4 is a diagram showing a pressure change on a contact surface which varies depending on whether or not the recess according to the embodiment of the present invention is present.

Next, the effect of the recess 107 shown in FIG. 2 reducing the pressure applied to the contact surface outer peripheral portion 117 was verified using a finite element method, and the result thereof will be described. FIG. 3 is a diagram showing a top surface of the rotor seal 104. FIG. 4 is a diagram showing a pressure change on the contact surface which varies depending on whether or not the recess 107 according to the embodiment of the present invention is present. FIG. 4 is a graph showing a value obtained by subtracting a pressure value of a structure where the recess 107 is not provided from a pressure value of a structure where the recess 107 is provided, the pressure being a surface pressure in an X direction in FIG. 3, that is, in an arrow direction moving from a center point O of the rotor seal 104 shown in FIG. 3 to the center of each of the through holes 101 positioned so as not to overlap the connection groove 103. The stator 102 is formed of stainless used steel (SUS), and the rotor seal 104 is formed of a resin material which is polyether-ether-ketone (PEEK). The horizontal axis represents a distance x from the center point O of the rotor seal 104 in the X direction in FIG. 3. The vertical axis represents a difference value in the pressure on the contact surface at the distance x. A range of x from about 1.1 mm to 1.4 mm corresponds to the through holes 101. Therefore, irrespective of whether or not the recess 107 is present, a force is not applied to the contact surface, and the surface pressure is zero. A range of x from about 1.75 mm to 2.2 mm corresponds to the outer peripheral portion of the contact surface between the stator 102 and the rotor seal 104. In this portion, in the structure where the recess 107 is provided, the surface pressure of the contact surface outer peripheral portion 117 is lower as compared to the structure where the recess 107 is not provided. That is, the rubbing phenomenon which occurs during the rotation of the seal can be reduced. Further, a range of x of about 1.1 mm or a range of x from 1.4 mm to 1.7 mm from the center point O, that is, the peripheral region of the through holes 101 which is a flow path exhibits a higher surface pressure in the structure where the recess 107 is provided than the structure where the recess 107 is not provided. This leads to improvement of sealing characteristics of the flow path. In addition, focusing on a surface pressure distribution, in the structure where the recess 107 is not provided, the surface pressure gradually increases toward the outer peripheral portion of the contact surface. However, in the structure where the recess 107 is provided, the surface pressure distribution is uniform as a whole. That is, according to the above-described configuration, the fastening load can be efficiently distributed in a plane. Accordingly, even when the fastening load is lower than that in the related art, sufficiently high sealing characteristics can be obtained. A reduction in the fastening load leads to a reduction in the power of a motor required to rotate the rotor seal 104, and it can also be expected that a structure of the motor will be simplified. When the surface pressure is uniform, it can be expected that a variation in the amount of wear in a radial direction will be reduced. Due to these effects, the product lifetime of the valve can be extended.

Figure 5:
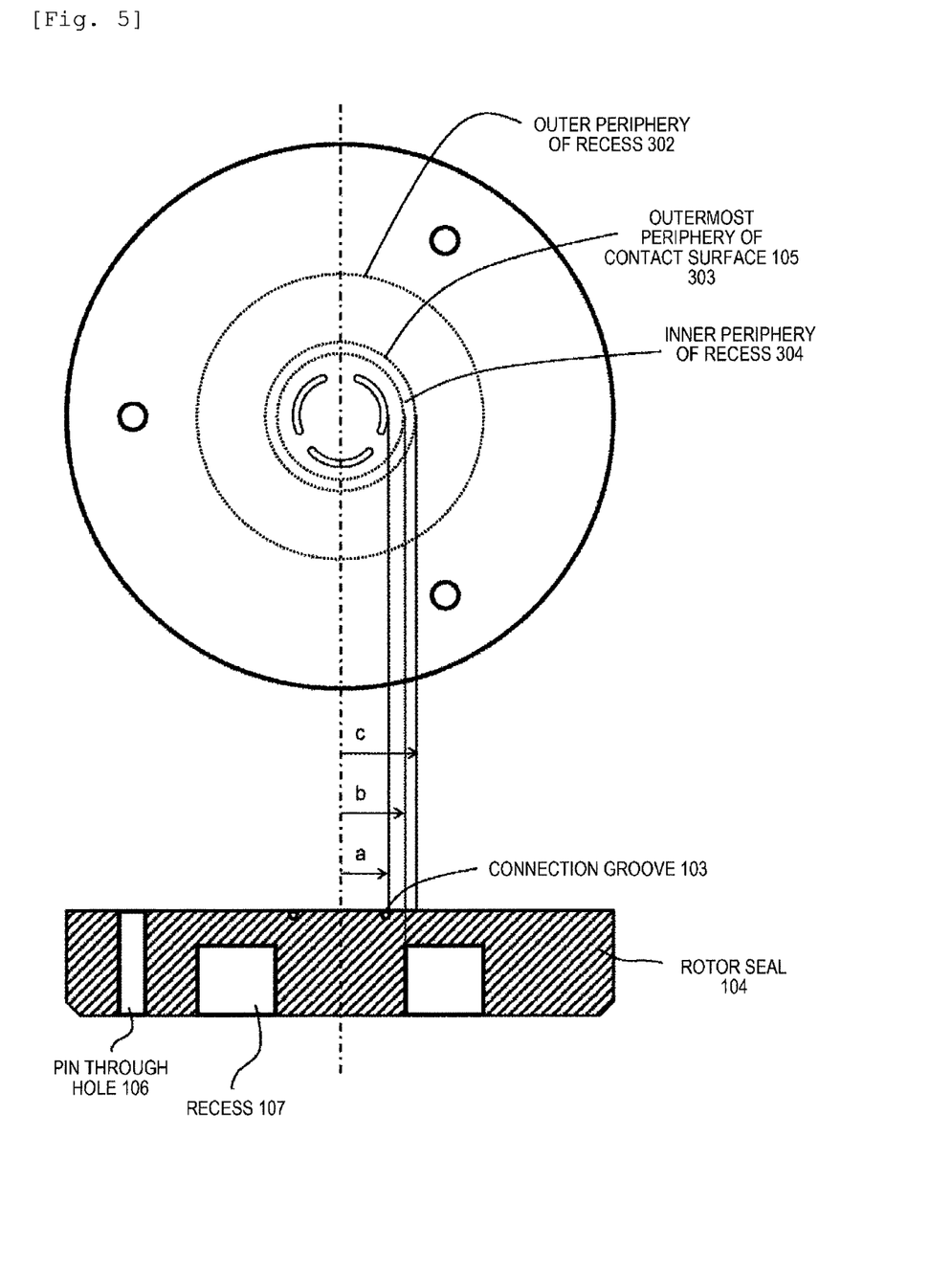
FIG. 5 is a diagram showing a positional relationship between an inner diameter of the recess according to the embodiment of the present invention, and a flow path and the contact surface.

Conditions of the configuration of the recess 107 which are effective to reduce the pressure applied to the contact surface outer peripheral portion 117 will be described using FIG. 5. FIG. 5 is a diagram showing a positional relationship between an inner diameter of the recess according to the embodiment of the present invention and a flow path and the contact surface. An outer diameter of the connection groove 103 is represented by a, an inner diameter of the recess is represented by b, and a diameter of an outermost periphery 303 of the contact surface 105 is represented by c. At this time, it is preferable that a≤b is satisfied because a sufficient pressure is necessary on the outside of the connection groove 103, which is the flow path, in order to prevent liquid leakage. In addition, it is preferable that b≤c is satisfied because the seal positioned outside the outermost periphery of the contact surface generates the load 203. That is, when the inner diameter b of the recess 107 is set so as to satisfy a≤b≤c, the surface pressure applied to the outer peripheral portion of the contact surface 105 can be efficiently reduced.

Figure 6:
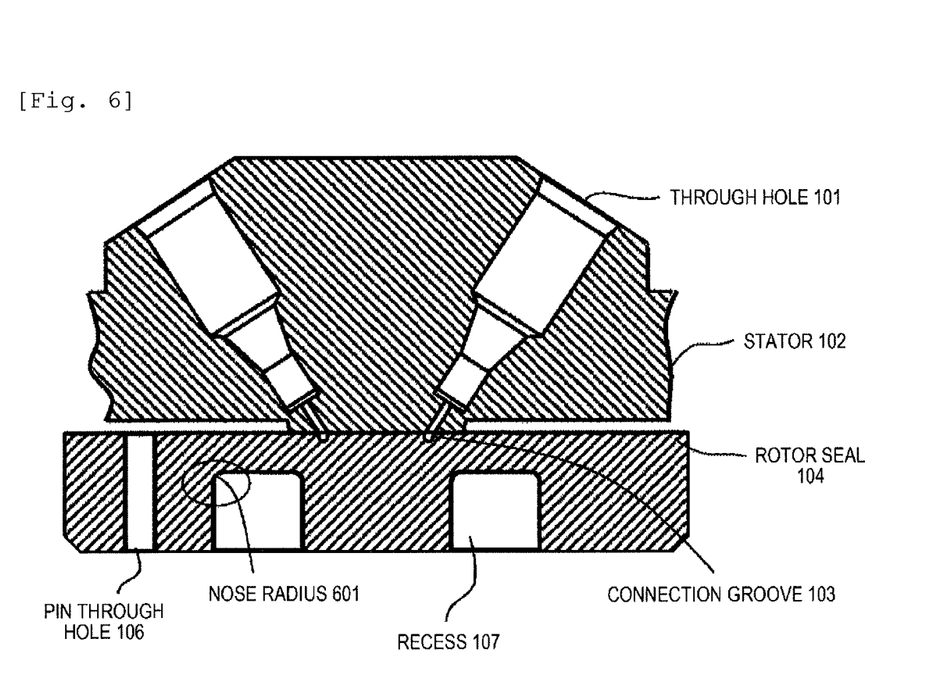
FIG. 6 is a diagram showing a configuration example (second example) of the fluid switching valve according to the embodiment (Embodiment 1) of the present invention.

The stator 102 and the rotor seal 104 can be freely selected according to the specification of the valve. The above-described pressure reduction effect does not depend on a combination between a material of the stator 102 and a material of the rotor seal 104. During the formation of the recess 107, in the case of a resin material such as PEEK, injection molding or cutting after molding is performed. In the case of a metal material such as SUS, cutting is performed. FIG. 6 is a diagram showing a configuration example (second example) of the fluid switching valve according to the embodiment (Embodiment 1) of the present invention. During the above-described cutting, a tool is used. Therefore, as in the recess 107 shown in the drawing, a nose radius 601, which is curved according to the tool, may be provided on a corner portion. In this way, during the processing, a position where the recess 107 is provided is not the contact surface containing the flow path. Therefore, high surface accuracy is not necessary, and the processing costs can be suppressed.

Embodiment 2

In this embodiment, various configurations of the recess of the fluid switching valve, which is effective to reduce the surface pressure applied to the contact surface outer peripheral portion 117, will be described.

Figure 7:
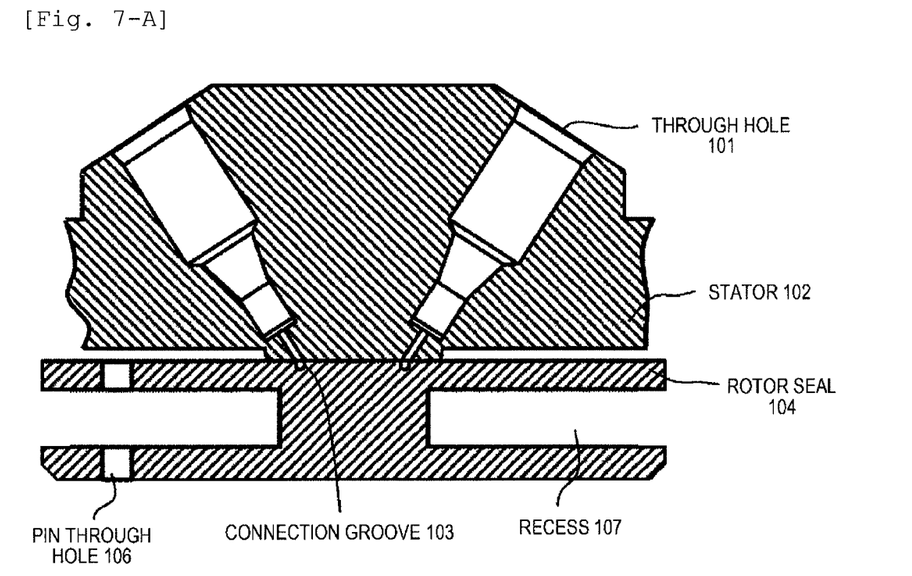

FIG. 7-A is a diagram showing a configuration example (third example) of the fluid switching valve according to the embodiment (Embodiment 2) of the present invention.

The description of portions having the same functions as the above-described components represented by the same reference numerals in the fluid switching valve 100 of FIG. 1 will not be repeated. In a case where the inner diameter of the recess 107 is set so as to satisfy the conditions described in Embodiment 1, the recess 107 may be formed on a side surface of the rotor seal 104 as shown in FIG. 7-A. Even in this case, the region that is present vertically downward with respect to the region containing at least the contact surface has higher rigidity than the other peripheral region. Therefore, the same surface pressure reduction effect as in Embodiment 1 can be obtained. In addition, with this method, the recess does not exist on the surface of the rotor seal 104 contacting the rotor 109. Therefore, the area of the contact surface between the rotor seal 104 and the rotor 109 increases, and contact stability is improved.

FIG. 7-B shows a configuration example (fourth example) in which the rotor seal 104 of FIG. 7-A is vertically divided into two portions and a shim member 118 is inserted between the two portions. According to the configuration shown in FIG. 7-B, each of the divided portions of the rotor seal is easily processible, and the costs can be reduced as compared to the configuration shown in FIG. 7-A. Further, the shim member 118 which is inserted between the two portions of the rotor seal member reduces inclination of the contact surface between the stator 102 and the rotor seal 104. As a result, a compressive force is uniformly distributed on the contact surface between the stator 102 and the rotor seal 104, and the sealability of the flow path can be maintained.

It is preferable that the shim member 118 is formed of a resin material such as PEEK having high compressive strength.

Figure 8:
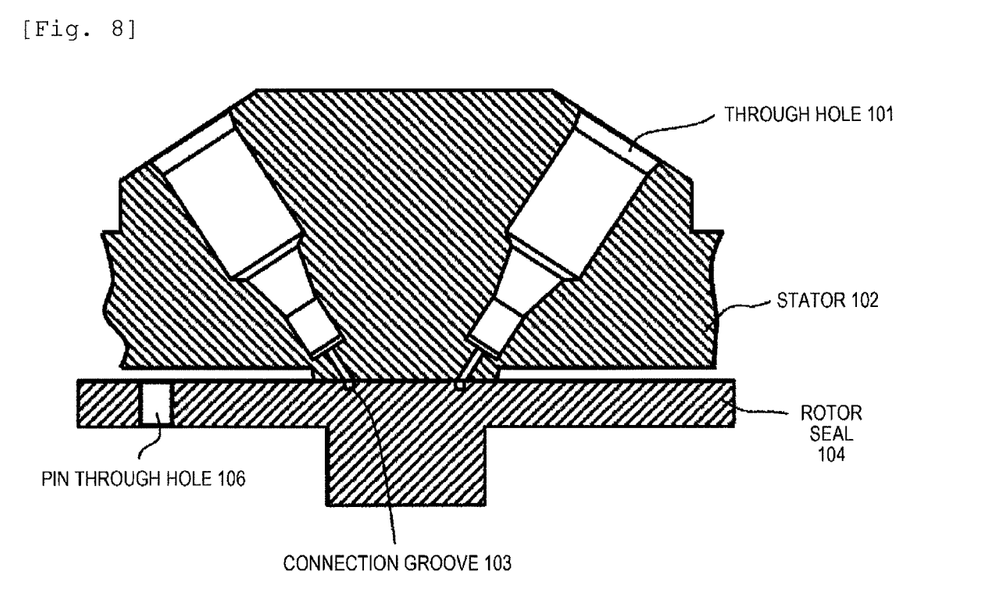
FIG. 8 is a diagram showing a configuration example (fifth example) of the fluid switching valve according to the embodiment (Embodiment 2) of the present invention.

FIG. 8 shows a configuration example (fifth example) of the fluid switching valve according to the embodiment (Embodiment 2) of the present invention. As shown in FIG. 8, a T-shaped structure may be adopted in which the portion of the rotor seal 104 that is present vertically downward with respect to the region containing at least the contact surface with the stator 102 remains by removing an outer peripheral region of the portion. When the rotor seal 104 formed of metal is used during cutting and the like, the method of removing the outer peripheral portion as shown in FIG. 8 is simpler than the method of adopting the groove shape as shown in FIG. 1 or 7. According to this configuration, a wide contact surface between the stator 102 and the rotor seal 104 can be secured, and thus it is easy to perform a surface treatment on the contact surface.

Figure 9:
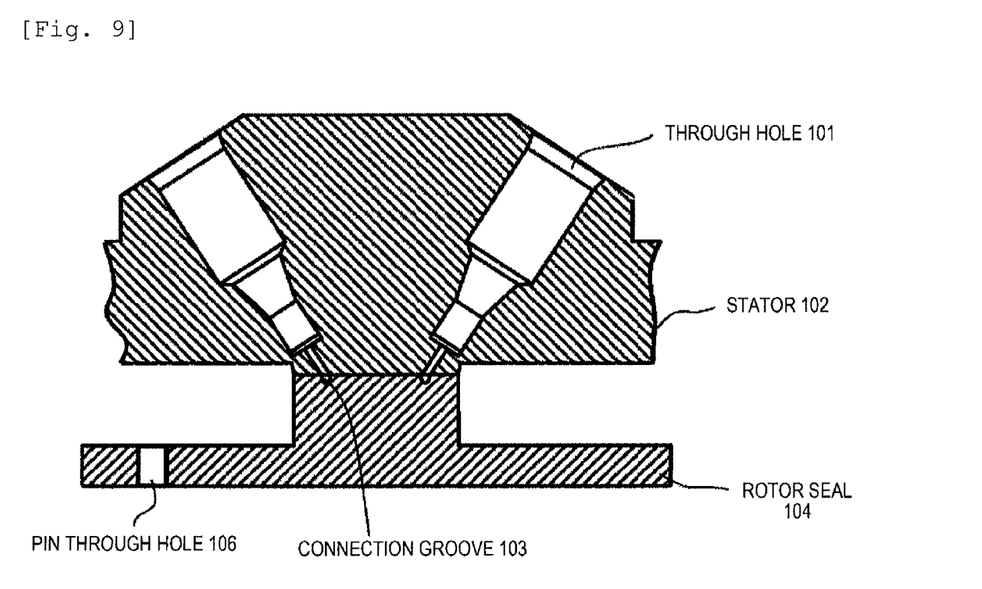
FIG. 9 is a diagram showing a configuration example (sixth example) of the fluid switching valve according to the embodiment (Embodiment 2) of the present invention.

FIG. 9 shows a configuration example (sixth example) of the fluid switching valve according to the embodiment (Embodiment 2) of the present invention. As shown in FIG. 9, an inverted T-shaped structure may be adopted in which the portion of the rotor seal 104 that is present vertically downward with respect to the region containing at least the contact surface with the stator 102 remains and a space is provided by removing an outer peripheral region of the portion. According to this configuration, a wide bottom surface of the rotor seal 104 can be secured, and thus stability is improved.

Figure 10:
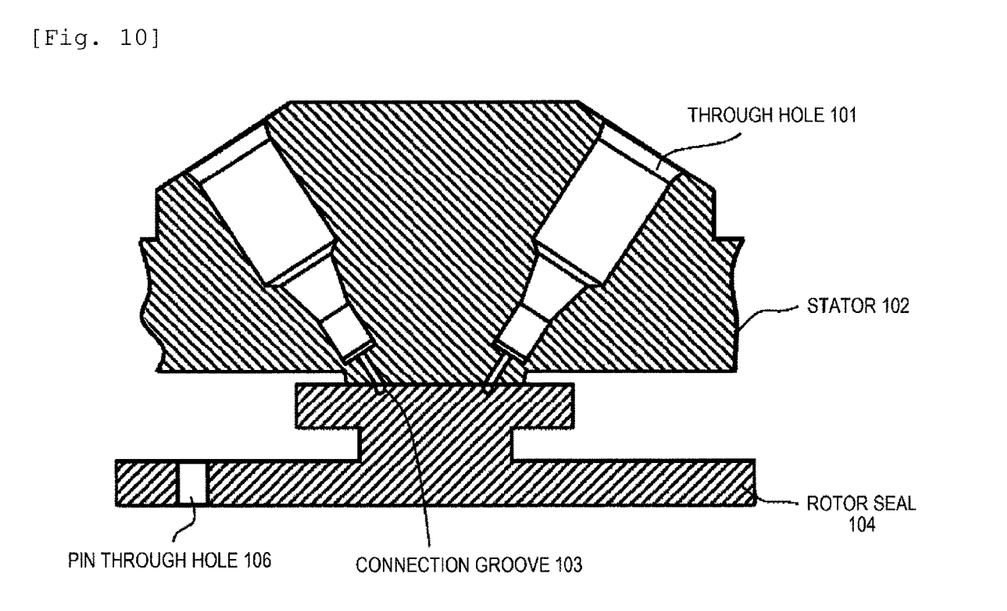
FIG. 10 is a diagram showing a configuration example (seventh example) of the fluid switching valve according to the embodiment (Embodiment 2) of the present invention.

FIG. 10 shows a configuration example (seventh example) of the fluid switching valve according to the embodiment (Embodiment 2) of the present invention. As shown in FIG. 10, a step may be provided to the recess. According to this configuration, it is easy to perform a surface treatment on the contact surface between the stator 102 and the rotor seal 104, and contact stability can be improved.

Figure 11:
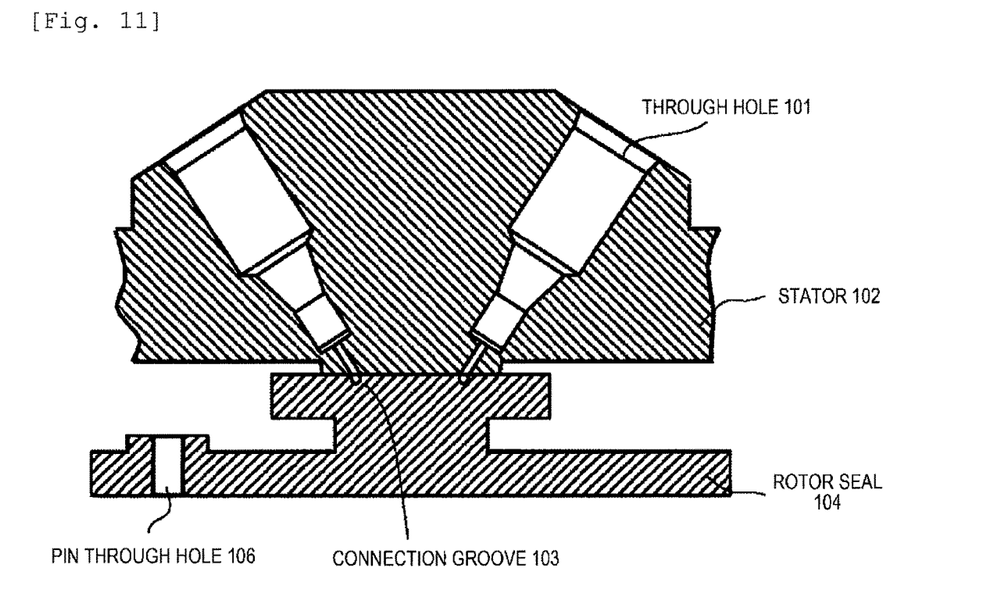
FIG. 11 is a diagram showing a configuration example (eighth example) of the fluid switching valve according to the embodiment (Embodiment 2) of the present invention.

FIG. 11 shows a configuration example (eighth example) of the fluid switching valve according to the embodiment (Embodiment 2) of the present invention. As shown in FIG. 11, a projection portion may be provided around the pin through hole 106. The rotor seal 104 is connected to the rotating rotor 109 through a pin which passes through the pin through hole 106. Therefore, reinforcement using the projection portion may be performed depending on the usage environment of the valve.

Figure 12:
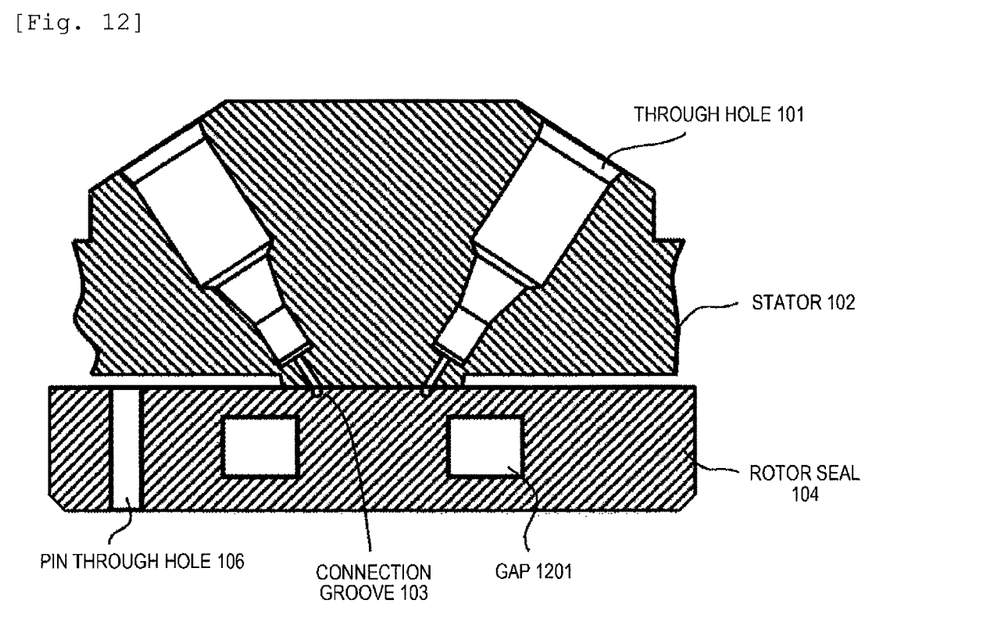
FIG. 12 is a diagram showing a configuration example (ninth example) of the fluid switching valve according to the embodiment (Embodiment 2) of the present invention.

FIG. 12 shows a configuration example (ninth example) of the fluid switching valve according to the embodiment (Embodiment 2) of the present invention. As shown in FIG. 12, a gap 1201 may be provided in the rotor seal 104. For example, a seal including the gap 1201 as shown in FIG. 12 can be manufactured by using additive manufacturing such as 3D printing.

Embodiment 3

In this embodiment, a configuration of a fluid switching valve in which regions having different rigidities are provided instead of the space of the recess 107 formed in the above-described examples will be described.

Figure 13:
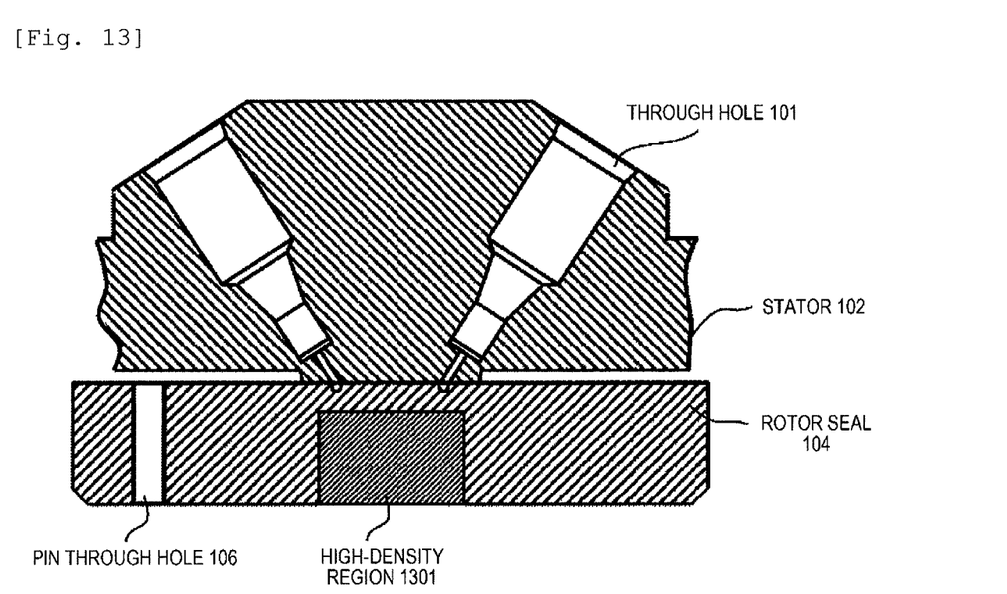
FIG. 13 is a diagram showing a configuration example (tenth example) of a fluid switching valve according to an embodiment (Embodiment 3) of the present invention.

FIG. 13 shows a configuration example (tenth example) of the fluid switching valve according to the embodiment (Embodiment 3) of the present invention. FIG. 13 shows an example of a configuration diagram of the fluid switching valve 100 according to Embodiment 3. In a region where rigidity is desired to be improved, a high-density region 1301 having a higher density than a material constituting the rotor seal 104 is provided. For example, in the case of a seal formed of a resin, the above-described configuration can be realized by filling the portion of the high-density region 1301 with the resin with a higher pressure than in the other regions.

Figure 14:
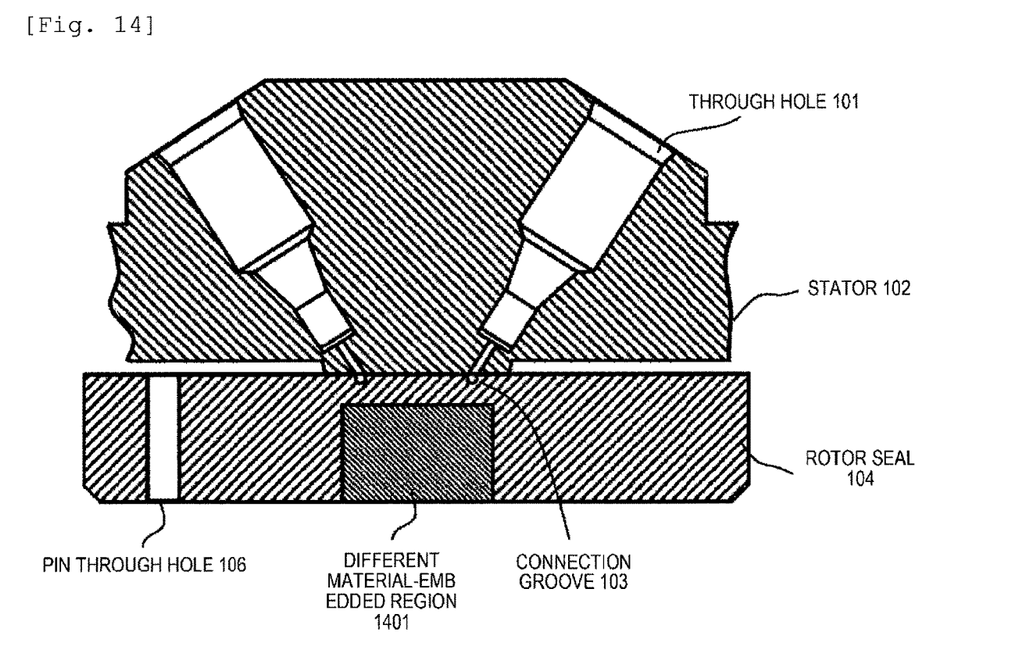
FIG. 14 is a diagram showing a configuration example (eleventh example) of the fluid switching valve according to the embodiment (Embodiment 3) of the present invention.

FIG. 14 shows a configuration example (eleventh example) of the fluid switching valve according to the embodiment (Embodiment 3) of the present invention. As shown in FIG. 14, a different material-embedded region 1401 may be provided by embedding an internal space of the rotor seal 104 with a different material from a material of the rotor seal 104. For example, the rigidity of the different material-embedded region 1401 can be improved to be higher than the other region by using a resin as the material of the rotor seal 104 and using SUS as the material of the different material-embedded region 1401. As an embedding method of the different material, various methods can be used, and examples thereof include a method of forming a recess in the rotor seal 104 in advance and embedding this recess with a different material. In addition, the different material-embedded region 1401 can be manufactured by preparing a material such as SUS as a different Material in advance and casting a resin material onto the vicinity of the different material.

Embodiment 4

In this embodiment, a configuration of a liquid chromatograph apparatus using the fluid switching valve 100 will be described.

Figure 15:
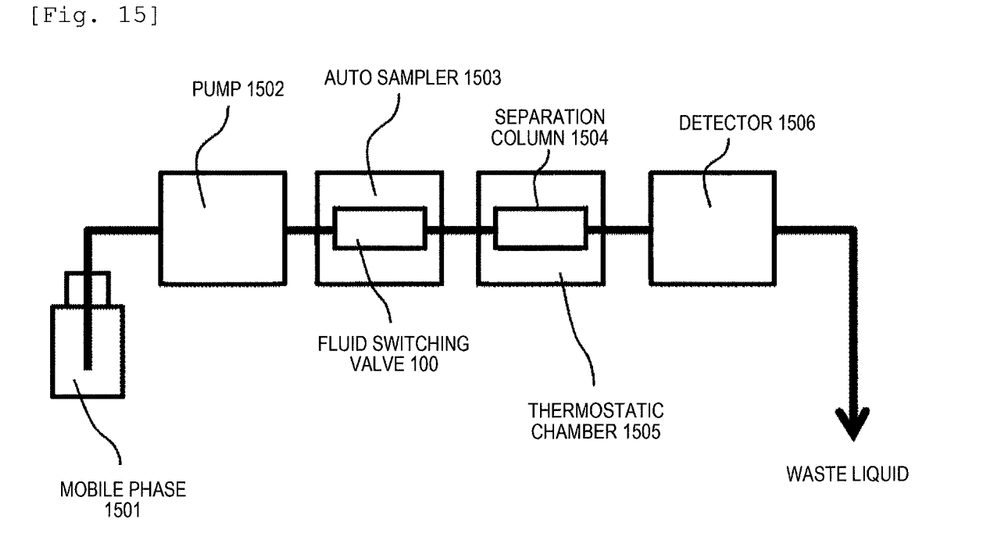
FIG. 15 is a diagram showing a configuration of a liquid chromatograph using the fluid switching valve according to an embodiment (Embodiment 4) of the present invention.

FIG. 15 is a block diagram showing the liquid chromatograph apparatus according to the embodiment of the present invention.

A mobile phase 1501 is fed to a separation column 1504 by a pump 1502. The separation column 1504 is arranged in a thermostatic chamber 1505. An auto sampler 1503 including the fluid switching valve 100 introduces a sample into a flow path of the mobile phase fed by the pump 1502. The fluid switching valve 100 causes the sample which is a separation object to flow into the separation column 1504 together with the mobile phase 1501. The sample and the mobile phase 1501 flowing into the separation column 1504 moves to a outflow side while repeating absorption/desorption for each component in the separation column 1504. As a result, each chemical component constituting the sample is separated.

Each component separated by the separation column 1504 is detected by a detector 1506.

According to the embodiment, the pressure applied to the contact surface outer peripheral portion 117 is reduced due to a difference in rigidity between the lower portion of the contact surface of the fluid switching valve 100 and the peripheral region around the lower portion. Therefore, the probability that the sample is erroneously detected by wear debris incorporating into the flow path is reduced. In addition, the occurrence of a rubbing phenomenon is reduced, and thus the replacement cycle of the valve can be extended. In this way, a fluid switching valve having superior detection performance and durability and a liquid chromatograph apparatus using the valve can be obtained.

The present invention is not limited to the above-described embodiments and includes various modification examples. For example, the above-described embodiments have been described in detail for easy understanding of the present invention and does not necessarily include all the configurations described above. In addition, a part of a configuration of an embodiment may be replaced with a configuration of another embodiment. Further, a configuration of an embodiment may be added to a configuration of another embodiment. In addition, regarding a part of the configuration of each of the embodiments, addition of another configuration, deletion, or replacement can be made.

REFERENCE SIGNS LIST

100: FLUID SWITCHING VALVE
101: THROUGH HOLE
102: STATOR
103: CONNECTION GROOVE
104: SEAL
105: CONTACT SURFACE
106: PIN THROUGH HOLE
107: RECESS
108: BEARING
109: ROTOR
110: HOUSING
111: PLATE SPRING
112: PLATE SPRING BEARING
113: BEARING
114: WASHER
115: HOUSING
116: NUT

117: CONTACT SURFACE OUTER PERIPHERAL PORTION
118: SHIM MEMBER
201: LOAD APPLIED TO CONTACT SURFACE FROM STATOR SIDE
202: LOAD APPLIED TO CONTACT SURFACE FROM SEAL SIDE
203: LOAD APPLIED TO CONTACT SURFACE OUTER PERIPHERAL PORTION
301: OUTER PERIPHERAL CONTACT PORTION OF THROUGH HOLE 101
302: OUTER PERIPHERY OF RECESS
303: OUTERMOST PERIPHERY OF CONTACT SURFACE 105
304: INNER PERIPHERY OF RECESS
601: NOSE RADIUS
1201: GAP
1301: HIGH-DENSITY REGION
1401: DIFFERENT MATERIAL-EMBEDDED REGION
1501: MOBILE PHASE
1502: PUMP
1503: AUTO SAMPLER
1504: SEPARATION COLUMN
1505: THERMOSTATIC CHAMBER
1506: DETECTOR

The invention claimed is:

1. A fluid switching valve comprising:
a stator having a plurality of through holes;
a rotating rotor; and
a seal having a connection groove through which the through holes are connected to each other,
wherein the seal includes
a first portion that is present vertically downward with respect to a region containing at least a contact surface with the stator, and
a second portion that is provided outside the first portion and has lower rigidity than the first portion, and
wherein
the second portion is formed by providing a groove on a surface of the seal other than a surface opposite to the stator,
the seal is connected to the rotating rotor with a pin that is inserted into a pin through hole, and
measured from a common origin
an inner diameter of the groove provided in the seal is equal to or greater than a diameter of the connection groove of the seal and is equal to or less than a diameter of the contact surface between the seal and the stator, and
a distance of the pin through hole from a center of the seal is greater than a diameter of the contact surface between the seal and the stator.

2. The fluid switching valve according to claim 1, wherein in the second portion, a space is provided in a region of the surface of the seal opposite to the stator excluding a region contacting the stator.

3. The fluid switching valve according to claim 2, wherein an outer diameter of the first portion is substantially equal to a diameter of the contact surface between the seal and the stator.

4. The fluid switching valve according to claim 3, wherein the second portion is formed of a resin material, the first portion is formed of a metal material.

5. The fluid switching valve according to claim 1, wherein the second portion is formed of a material different from a material of the first portion.

6. A liquid sample introducing apparatus comprising a fluid switching valve,
the fluid switching valve including:
a rotating rotor;
a stator having a plurality of through holes; and
a seal having a connection groove through which the through holes are connected to each other,
wherein the seal includes
a first portion that is present vertically downward with respect to a region containing at least a contact surface with the stator, and
a second portion that is provided outside the first portion and has lower rigidity than the first portion, wherein
the second portion is formed by providing a groove on a surface of the seal other than a surface opposite to the stator,
the seal is connected to the rotating rotor with a pin that is inserted into a pin through hole, and
measured from a common origin
an inner diameter of the groove provided in the seal is equal to or greater than a diameter of the connection groove of the seal and is equal to or less than a diameter of the contact surface between the seal and the stator, and
a distance of the pin through hole from a center of the seal is greater than a diameter of the contact surface between the seal and the stator.

7. A liquid chromatograph apparatus comprising a fluid switching valve,
the fluid switching valve including:
a rotating rotor;
a stator having a plurality of through holes; and
a seal having a connection groove through which the through holes are connected to each other,
wherein the seal includes
a first portion that is present vertically downward with respect to a region containing at least a contact surface with the stator, and
a second portion that is provided outside the first portion and has lower rigidity than the first portion, wherein
the second portion is formed by providing a groove on a surface of the seal other than a surface opposite to the stator, and
the seal is connected to the rotating rotor with a pin that is inserted into a pin through hole, and
measured from a common origin
an inner diameter of the groove provided in the seal is equal to or greater than a diameter of the connection groove of the seal and is equal to or less than a diameter of the contact surface between the seal and the stator, and
a distance of the pin through hole from a center of the seal is greater than a diameter of the contact surface between the seal and the stator.

* * * * *